(12) United States Patent
Adler

(10) Patent No.: US 11,633,252 B2
(45) Date of Patent: Apr. 25, 2023

(54) CARRYING CASE FOR STERILE OBJECTS

(71) Applicant: Cases By Source Inc., Mahwah, NJ (US)

(72) Inventor: Matthew L. Adler, Mahwah, NJ (US)

(73) Assignee: Cases By Source Inc., Mahwah, NJ (US)

(*) Notice: Subject to any disclaimer, the term of this patent is extended or adjusted under 35 U.S.C. 154(b) by 60 days.

(21) Appl. No.: 17/136,729

(22) Filed: Dec. 29, 2020

(65) Prior Publication Data

US 2021/0113289 A1    Apr. 22, 2021

Related U.S. Application Data

(63) Continuation-in-part of application No. 15/970,187, filed on May 3, 2018, now abandoned.

(60) Provisional application No. 62/500,606, filed on May 3, 2017.

(51) Int. Cl.

| | |
|---|---|
| *A61B 50/31* | (2016.01) |
| *A45C 13/02* | (2006.01) |
| *A45C 13/10* | (2006.01) |
| *A45C 5/02* | (2006.01) |
| *A61B 50/00* | (2016.01) |
| *A61B 50/30* | (2016.01) |

(52) U.S. Cl.
CPC .............. *A61B 50/31* (2016.02); *A45C 5/02* (2013.01); *A45C 13/02* (2013.01); *A45C 13/103* (2013.01); *A45C 2013/026* (2013.01); *A61B 2050/0088* (2016.02); *A61B 2050/3008* (2016.02); *A61B 2050/311* (2016.02)

(58) Field of Classification Search
CPC ............ A61B 50/31; A61B 2050/0088; A61B 2050/311; A45C 13/02; A45C 13/103; A45C 2013/026
USPC ........ 206/438, 561; 220/511, 554, 544, 512, 220/510, 528, 529, 507; 221/126.8, 221/126.9, 133.2, 133.5, 90.03
See application file for complete search history.

(56) References Cited

U.S. PATENT DOCUMENTS

| | | | | |
|---|---|---|---|---|
| 401,439 A | * | 4/1889 | Karo .................... | A45C 13/02 190/36 |
| 2,740,546 A | * | 4/1956 | Kowalski ............. | B65D 25/108 211/74 |
| 3,160,306 A | * | 12/1964 | Smalley ............... | B65D 85/305 220/512 |
| 4,099,656 A | | 7/1978 | Newmann | |

(Continued)

*Primary Examiner* — Chun Hoi Cheung
(74) *Attorney, Agent, or Firm* — John H. Choi & Associates

(57) ABSTRACT

A carrying case includes an outer container with a plurality of side walls extending from a lower support. An outer lid is at least partially removably coupled with the plurality of side walls and positioned opposite the lower support. Each of the side walls, lower support and outer lid have an inner surface defining an interior space within the case. A plurality of first attachment means extend from at least two opposing side wall inner surfaces. A removable inner tray includes a plurality of inserts configured to fit within the interior space of the outer container. A plurality of second attachment means extend from the plurality of inserts and are positioned to correspond with locations of the first attachment means, such that the first and second attachment means are engaged when the inner tray is positioned within the interior space of the case.

19 Claims, 10 Drawing Sheets

(56) References Cited

U.S. PATENT DOCUMENTS

| | | | |
|---|---|---|---|
| 4,499,997 A * | 2/1985 | Swingley, Jr. | B65D 81/261 206/427 |
| 5,173,273 A * | 12/1992 | Brewer | A61L 2/26 422/300 |
| 5,174,453 A * | 12/1992 | Stoeffler | A61B 50/33 206/439 |
| 5,333,751 A * | 8/1994 | Santucci, Sr. | B65D 25/108 229/120.32 |
| 6,050,412 A | 4/2000 | Clough | |
| 6,146,673 A * | 11/2000 | Ferguson | B65D 25/108 220/660 |
| 6,153,237 A * | 11/2000 | Ferguson | B65D 25/108 220/660 |
| 6,186,351 B1 * | 2/2001 | Coyle | F25D 3/08 220/23.88 |
| 6,622,864 B1 | 9/2003 | Debbs | |
| 7,395,929 B2 | 7/2008 | Keffeler | |
| 7,597,209 B2 | 10/2009 | Rothschild | |
| 7,780,016 B1 * | 8/2010 | Cornwell | B25H 3/003 211/69 |
| 7,861,552 B1 * | 1/2011 | Hughes | A45C 13/02 62/457.2 |
| 7,934,494 B1 * | 5/2011 | Schneider | A47J 33/00 126/30 |
| 8,668,082 B2 | 3/2014 | Greene | |
| 9,250,950 B2 | 2/2016 | Archer et al. | |
| 9,694,489 B2 * | 7/2017 | Steele | B65D 25/205 |
| 2002/0126920 A1 * | 9/2002 | Mogil | A45C 7/0077 383/110 |
| 2007/0074991 A1 | 4/2007 | Heisserer | |
| 2007/0084742 A1 | 4/2007 | Miller | |
| 2008/0237325 A1 | 10/2008 | Mittelstaedt | |
| 2011/0017624 A1 | 1/2011 | Robertson | |
| 2011/0049138 A1 * | 3/2011 | Korczak | A45C 13/008 220/2 |
| 2011/0154889 A1 | 7/2011 | Stafford | |
| 2013/0168441 A1 | 7/2013 | Landgrebe | |
| 2013/0277262 A1 | 10/2013 | Nemard | |
| 2013/0310802 A1 | 11/2013 | Weinmann | |
| 2014/0216966 A1 | 8/2014 | Ramkhelawan | |
| 2016/0023349 A1 | 1/2016 | Hoppe | |
| 2017/0021046 A1 | 1/2017 | Drake | |
| 2018/0265256 A1 | 9/2018 | Fisher, Jr. | |

\* cited by examiner

CARRYING CASE FOR STERILE OBJECTS

CROSS-REFERENCE TO RELATED APPLICATION

This application is a continuation-in-part of U.S. application Ser. No. 15/970,187, filed on May 3, 2018, which claims priority to U.S. Provisional Application No. 62/500,606, filed on May 3, 2017, both of which are incorporated by reference in their entireties.

FIELD

The present disclosure relates to cases, in particular to carrying cases for storing and transporting sterile objects.

BACKGROUND

Bags with partitions are often used by medical device sales representatives, such as orthopedic device sales representatives, to carry, maintain inventory, and deliver boxed and sterile packages, implants or devices for use at the point of care during surgery. These bags are typically soft bags made of fabric material with dividers made of plastic supported by foam.

These bags are sometimes moved into operating rooms, creating a risk of contamination of the bags' contents as well as the environment due to the nature of the fabric material and polymers used in their manufacture. In addition, these materials may not be able to be cleaned effectively and the materials themselves may not be safe for use in the operating room.

Therefore, often times, the carrying bags of the prior art are prohibited from entering into a sterile environment such as a hospital operating room. Instead, the contents therein are handled separately from the bag and independently transported into the sterile environment. Such a process is not only time-consuming but also requires additional work to track the contents.

In addition, the task at hand within the sterile environment is delayed when a need arises for a part that is not present in the sterile environment. For example, a surgeon may need a part of a different size during surgery. If that particular part is not already in the operating room, one must leave the operating room, locate the part, ensure that the part meets the sterilization requirements and transport the part into the operating room.

Therefore, a need exists for a case capable of transporting sterile objects, including transporting entire cases or trays of the sterile objects into a sterile environment, while minimizing the risk of contamination of the sterile environment.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The case of the present invention solves the problems of the prior art and provides additional advantages.

The case of the present invention comprises: (i) an outer container, having at least one lid and at least one base; (ii) a optional tamper-proof seal coupled to said lid; (iii) a removable inner tray made of thermoplastic polymer; and (iv) a handle coupled to said inner tray. The tray in the present invention is made from wipeable foam dividers wrapped in a foam tub which drastically improves cleanability/wipeability. The wipeable foam dividers may be composed of polypropylene foam, either with or without a foam wrap.

In one embodiment, the outer container is constructed of a polymeric material capable of being wiped and/or sanitized. Thus, the outer container is sanitized and transported in its entirety into a sterile environment. Therefore, a user is provided with a greater selection of items since the user could have access to the entire contents of the case.

The present invention also provides a method for preparing the case comprising the steps of: (i) cleaning the tray and the inside of the outer container; (ii) placing the tray in the container; (iii) placing objects in the tray; (iv) securing the lid to the outer container; and (v) applying a tamper-proof seal.

The present invention also provides a method for using the case comprising the steps of: (i) removing an optional tamper-proof seal; (ii) opening the lid; (iii) removing the tray; and (iv) transporting the tray to the final destination. The method of the present invention includes taking the case into the operating room (OR) environment, with the case containing the tray with the dividers and the implants into the OR after cleaning the case and its contents.

The material and design of the case with the removable tray make it lightweight, enable easy and effective cleaning, and minimize the risk of contamination. In an operating room environment, where speed and cleanliness are crucial, this provides faster access to required medical equipment while minimizing the risk to patients. The case would also be valuable in research and forensic laboratory environments where contamination is a major concern.

In one embodiment, the present invention is a carrying case comprising: an outer container having an outer lid; a first tamper-proof seal coupled to the outer lid; a removable inner tray having a compartment for holding an object; and an inner handle coupled to the inner tray. The outer container is composed of a material selected from a polymeric material, fabric coated with a polymeric material, metal, and/or a composite material. The polymeric material is selected from silicone, plastic, and vinyl. The metal includes aluminum and stainless steel. The outer container may have a waterproof wipeable interior surface. The carrying case optionally includes an outer handle coupled to an outer surface of the outer container. The carrying case optionally includes a carrying strap coupled to an outer surface of the outer container. The carrying case optionally includes a roller coupled to an outer surface of the outer container. The optional tamper-proof seal is selected from an adhesive tape and an airtight zipper. The removable inner tray includes: a bottom surface; and a plurality of side walls coupled to the bottom surface. The carrying case optionally includes a divider forming a plurality of compartments for respectively storing a plurality of objects. Each compartment includes an inner lid coupled to a second tamper-proof seal. The removable inner tray is composed of material selected from a polypropylene foam, a thermoplastic polymer, a metal, or silicone.

In another embodiment, the present invention is a method comprising: providing a case with an outer container, a tray, an outer lid, and an optional first tamper-proof seal; cleaning the tray and inside of the outer container; placing the tray in the outer container; placing an object in the tray; securing the outer lid to the outer container; and may include applying the first tamper-proof seal to the lid. The method optionally includes forming a plurality of compartments for respectively storing a plurality of objects using a divider, providing an inner lid for each compartment, and sealing the inner lid with an optional second tamper-proof seal.

In an alternative embodiment, the present invention is method comprising: providing a case with an outer container, a tray, an outer lid, and a first tamper-proof seal, wherein the tray holds an object; removing the first tamper-proof seal from the outer lid; opening the outer lid; removing the tray with the object; and transporting the tray with the object to a destination. The method optionally includes forming a plurality of compartments for respectively storing a plurality of objects using a divider; and removing a selected object from a respective compartment, as well as providing an inner lid for each compartment; and unsealing a selected inner lid with a second tamper-proof seal to remove the selected object.

In another embodiment, the present invention provides a carrying case comprising an outer container having a plurality of side walls extending from a lower support; an outer lid at least partially removably coupled with the plurality of side walls and positioned opposite the lower support, each of the side walls, lower support and outer lid having an inner surface and an outer surface, the inner surfaces of the side walls, lower support and outer lid defining an interior space within the case; and a plurality of first attachment means extending from at least two opposing side wall inner surfaces. The carrying case also comprises a removable inner tray having a plurality of inserts, the plurality of inserts configured to fit within the enclosed space of the outer container; and a plurality of second attachment means extending from the plurality of inserts, each of the second attachment means positioned to correspond with locations of the first attachment means such that the first and second attachment means are engaged when the inner tray is positioned within the interior space of the case. The first attachment means is a loop formed with a flexible fabric material and the second attachment is a hook. The outer lid is coupled with the plurality of side walls by a water-resistant zipper. The outer container is composed of a material selected from a polymeric material, metal, and/or a composite material, wherein the polymeric material is selected from silicone, plastic, and vinyl and wherein the metal is selected from aluminum and stainless steel. The inner surfaces of the side walls, lower support and outer lid are water-resistant and shed-resistant. The outer surface of the outer container is constructed of a water-resistant material. The carrying case also includes an outer handle coupled to the outer surface of the outer container and a carrying strap coupled to the outer surface of the outer container. Finally, the inner tray is constructed of a coated metal.

BRIEF DESCRIPTION OF DRAWINGS

The foregoing summary, as well as the following detailed description of presently preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

Figure 1:
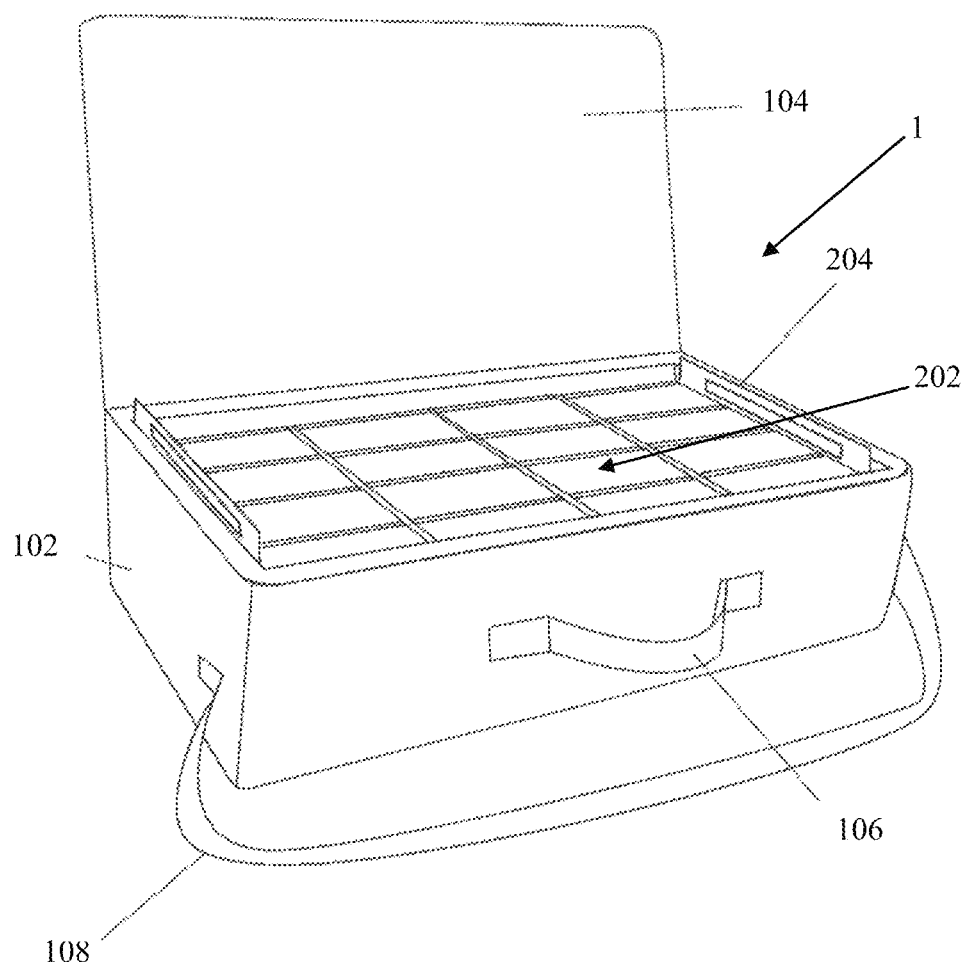
FIG. 1 is a perspective view of the case of the present invention.

To facilitate an understanding of the invention, identical reference numerals have been used, when appropriate, to designate the same or similar elements that are common to the figures. Further, unless stated otherwise, the features shown in the figures are not drawn to scale and are shown for illustrative purposes only.

DETAILED DESCRIPTION

Certain terminology is used in the following description for convenience only and is not limiting. The article "a" is intended to include one or more items, and where only one item is intended the term "one" or similar language is used. Additionally, to assist in the description of the present invention, words such as top, bottom, side, upper, lower, front, rear, inner, outer, right and left are used to describe the accompanying figures. The terminology includes the words above specifically mentioned, derivatives thereof, and words of similar import.

Referring to FIG. 1, the case 1 of the present invention comprises: (i) an outer container 102, having a lid 104; (ii) an optional tamper-proof seal (not shown) coupled to said lid 104; and (iii) a removable inner tray 202, having a handle 204.

In the exemplar embodiment, the outer container 102 is made of a polymeric material such as silicone or plastic, with a waterproof interior surface that can be cleaned. The polymeric material enables the container 102 to be lightweight, comfortable to carry, easy to clean, and allows for a lid 104 without a separate hinge component. In other embodiments, the outer container 102 is made of metal or metal alloy such as stainless steel, or a composite material.

In the exemplar embodiment, an outer handle 106 is coupled to the outer container 102 as well as a carrying strap 108 to facilitate transport. Optionally, rollers could be operably coupled to the outer container 102 on an outer surface thereof to further assist a user for transport.

The optional tamper-proof seal (not shown) can be used to secure the lid 104 of the outer container 102 in a closed position (not shown) and would provide a visual indication of whether the lid 104 has been opened. The tamper-proof seal may be an adhesive tape that must be removed or severed to open the lid 104. This ensures that the contents of the container 102 are not exposed to the outside environment prior to its intended use.

Alternatively, the optional tamper-proof seal could be an airtight zipper having means for securing the zipper closed. For example, the zipper could include one or more pull tabs having holes so that a lock, e.g., combination lock, key lock or zip tie, could be secured to holes of adjacent pull tabs or between one pull tab and another engagement on the outer portion of the outer container 102.

Figure 2:
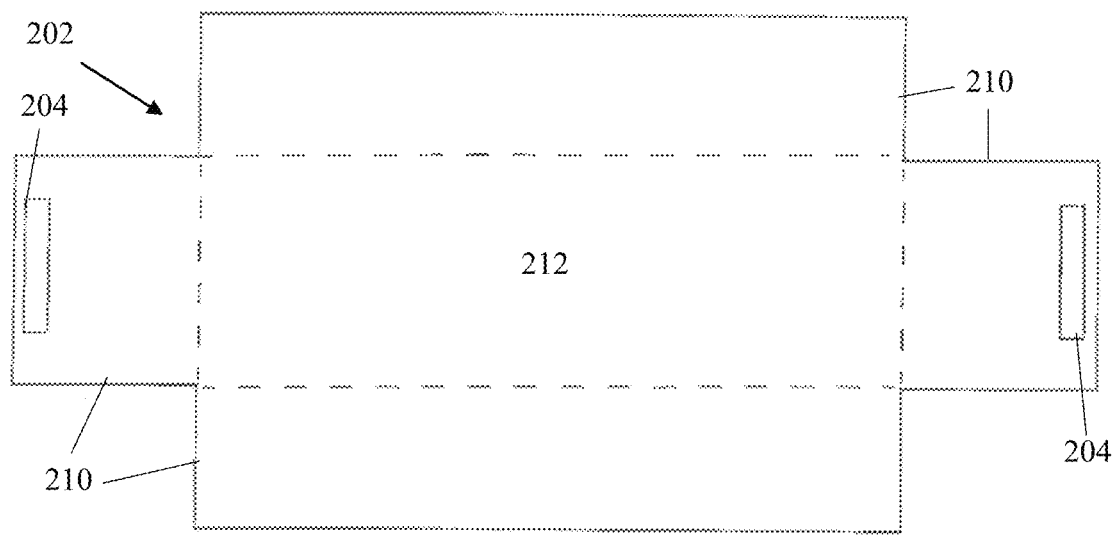
FIG. 2 is a plan view of the tray of the present invention in an unfolded configuration.
Figure 3:
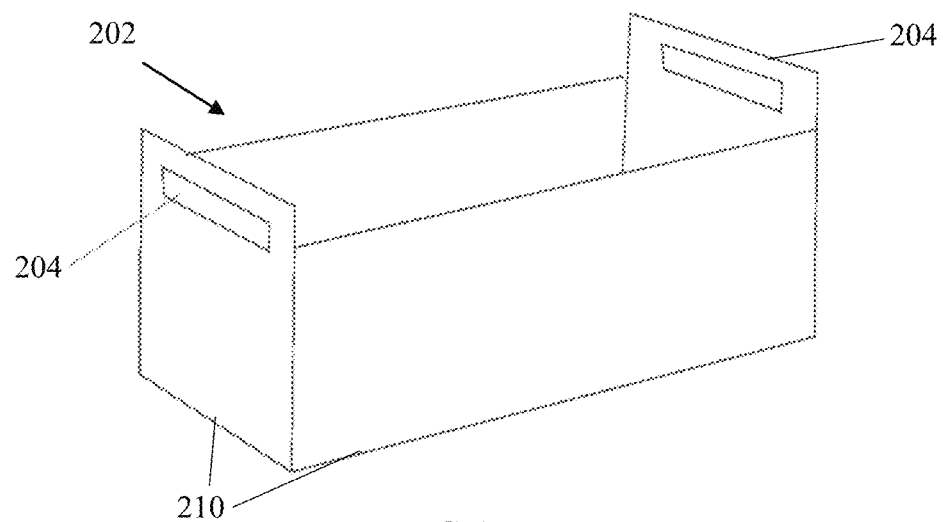
FIG. 3 is a perspective view of the tray of the present invention in a folded configuration.

Referring to FIGS. 1-4, the case 1 of the present invention includes a removable inner tray 202 having a plurality of side walls or surfaces 210 coupled to a bottom surface 212. Referring to FIG. 2, in the exemplar embodiment, the side walls or surfaces 210 of the tray 202 can be unfolded to be planar to the bottom surface, creating a single flat surface for easier cleaning. When folded, as shown in FIG. 3, the walls 210 are coupled together by heat welding, adhesive or by fasteners, for example, hook-and-loop, and snap buttons in combination with straps. The removable inner tray 202 also includes at least one handle 204 integral to at least one wall 210 to allow the tray 202 to be easily removed from the container 102.

Figure 4:
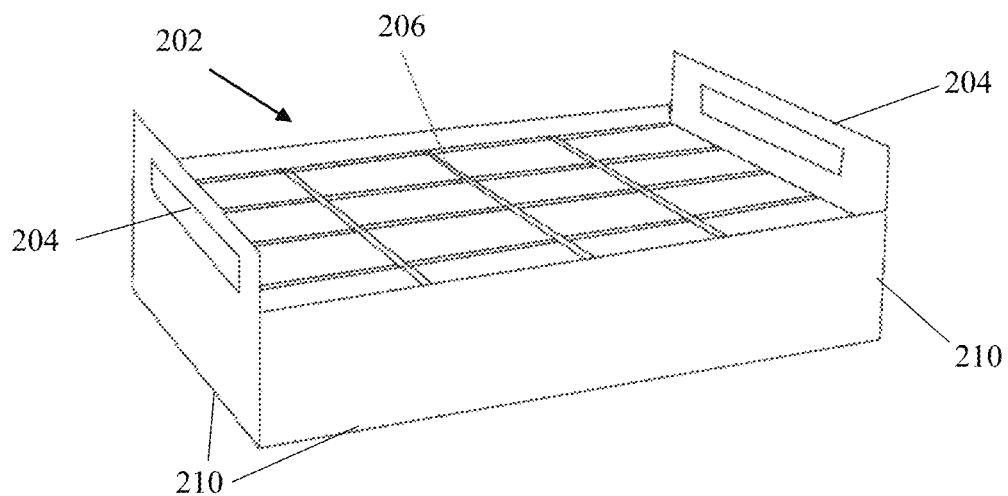
FIG. 4 is a perspective view of the tray of the present invention with dividers installed therein.
Figure 5:
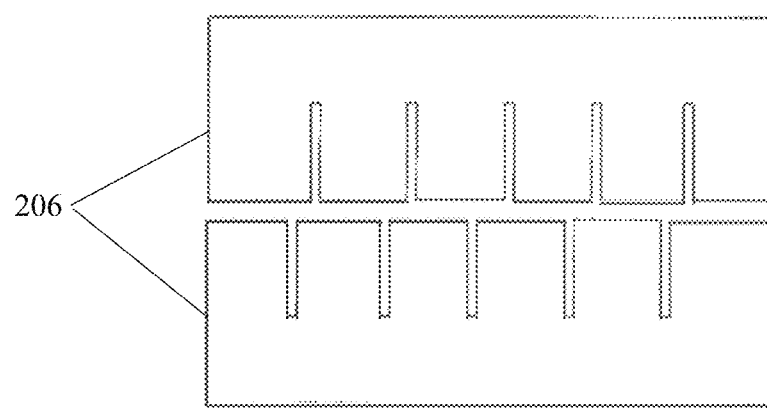
FIG. 5 are plan views of the dividers of the present invention.

Referring to FIGS. 4-5, the removable inner tray 202 also includes one or more compartments for storing sterilized objects. In the exemplar embodiment, the removable inner tray 202 further comprises one or more dividers 206 to form a plurality of compartments. The dividers 206 may be integral to the tray 202 or removable for easier cleaning. Each divider 206 may have one or more notches enabling dividers 206 to intersect each other, creating additional compartments. The dividers 206 can be arranged in multiple configurations to form compartments of varying sizes.

In another embodiment, each compartment comprises a lid coupled to a tamper-proof seal. This enables individual objects to be removed from the compartments without the risk of contaminating the other objects.

Alternatively, the case 1 could be provided with multiple inner trays. For example, the case 1 could include inner trays stacked on top of each other to accommodate for quantity or size of the content within the case 1. As a further alternative, the case 1 could be provided with multiple compartments, with each compartment having its own inner tray. For example, an upper compartment could be separated from a lower compartment with an intermediate floor between the compartments while each compartment is accessed by a separate tamper-proof seal.

In the exemplar embodiment, the removable inner tray 202 is made of polypropylene foam. The material is lightweight, safe for operating room use, easily cleaned, and does not have any stray fibers that can enter the sterile field. In other embodiments, the removable inner tray 202 is made of silicone, a thermoplastic polymer, or metal.

Referring to the method for preparing the case, the method comprises the steps of: (i) cleaning the tray and the inside of the outer container; (ii) placing the tray in the container; (iii) placing objects in the tray; (iv) closing the lid; and (v) optionally applying a tamper-proof seal.

In the exemplar embodiment, the inside of the outer container 102 and the removable inner tray 202 are cleaned by hand or machine and the tray 202 is placed in the container 102. Sterile objects, such as medical implants, are placed in the tray 202. The lid 104 of the container 102 is closed and a tamper-proof seal is applied to hold the lid 104 closed. The container 102 can then be transported or stored to maintain inventory.

Referring to the method for using the case 1, the method comprises the steps of: (i) removing the tamper-proof seal; (ii) opening the lid 104; (iii) removing the tray 202; and (iv) transporting the tray 202 to the final destination.

At the point of use, the optional tamper-proof seal if used is broken, the lid 104 of the outer container 102 is opened, the removable inner tray 202 is removed, and the tray 202 is transported to the final destination, such as an operating room. This ensures that only the tray 202 and its contents are transported and not the container 102, which had been exposed to the outside environment and possibly contaminated.

In another embodiment, the outer container 102 is made of material that can be easily and effectively cleaned. The outer container 102 is cleaned prior to transport into a sterile environment. Thus, the entire case 1 and its contents therein are available in the sterile environment.

The case 1 is cleaned and sanitized by methods known in the art. These methods include the methods specified in the Guideline for Disinfection and Sterilization in Healthcare Facilities published by the Center for Disease Control of the U.S. Department of Health and Human Services, which is incorporated herein by reference.

Figure 6:
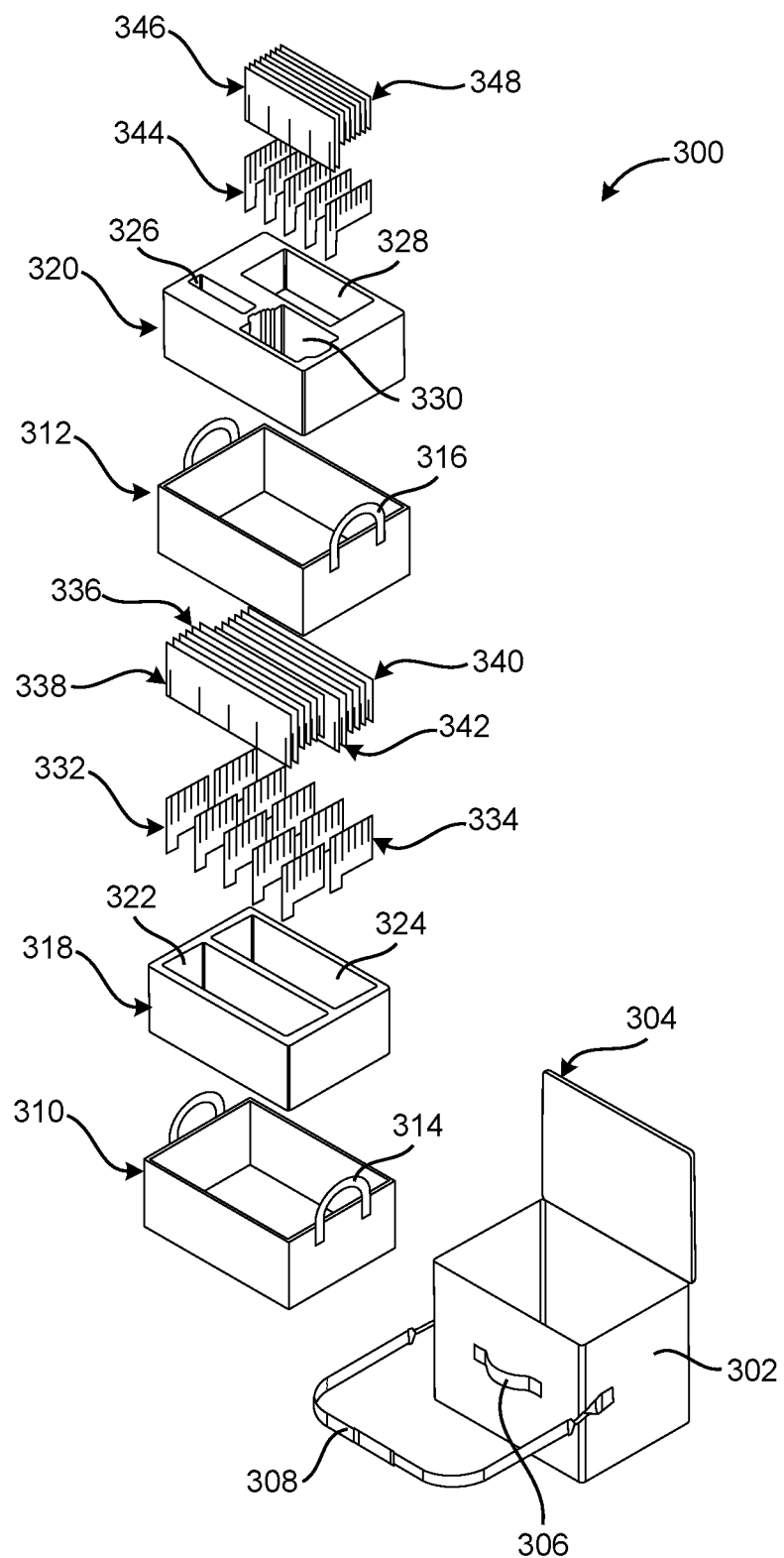
FIG. 6 is a top front perspective view of an alternative embodiment of the case of the present invention with parts separated.

In an alternative embodiment, shown in FIG. 6, a case 300 includes an outer container 302 which is composed of vinyl, although other materials may be used such as silicone and plastic. Alternatively, the outer container 302 may be composed of a layer of materials, with an exterior material composed of vinyl, and an interior material composed of nylon. Other known materials may be used for the outer container 302. The outer container 302 has an outer lid 304 which may be connected to the outer container 302 by a hinge or other types of fasteners. A tamper-proof seal may optionally be used to removably seal the outer lid 304 to the outer container 302. The outer container 302 may optionally include a handle 306 and/or a carrying strap 308.

At least one tray 310, 312 is provided which is shaped and dimensioned to fit inside the outer container 302. Each tray 310, 312 may optionally include at least one handle 314, 316, respectively, for manipulating and inserting or removing the trays 310, 312 into or out of the outer container 302. Each tray 310, 312 may be a corrugated box composed of plastic or other materials. Furthermore, at least one insert 318, 320 is provided which is shaped and dimensioned to fit inside a tray 310, 312, respectively. Each insert 318, 320 may be composed of polyethylene (PE) foam or other known materials, and each insert 318, 320 may include at least one compartment 322-330, respectively, which are shaped and dimensioned for receiving sterilized objects.

In addition, each of the compartments 322-330 may be shaped and dimensioned to receive dividers 332-348, respectively, which may be composed of polypropylene (PP) foam or other known materials, for further subdividing respective compartments 322-330 laterally and/or longitudinally into sub-compartments for individually receiving sterilized objects.

Figure 7:
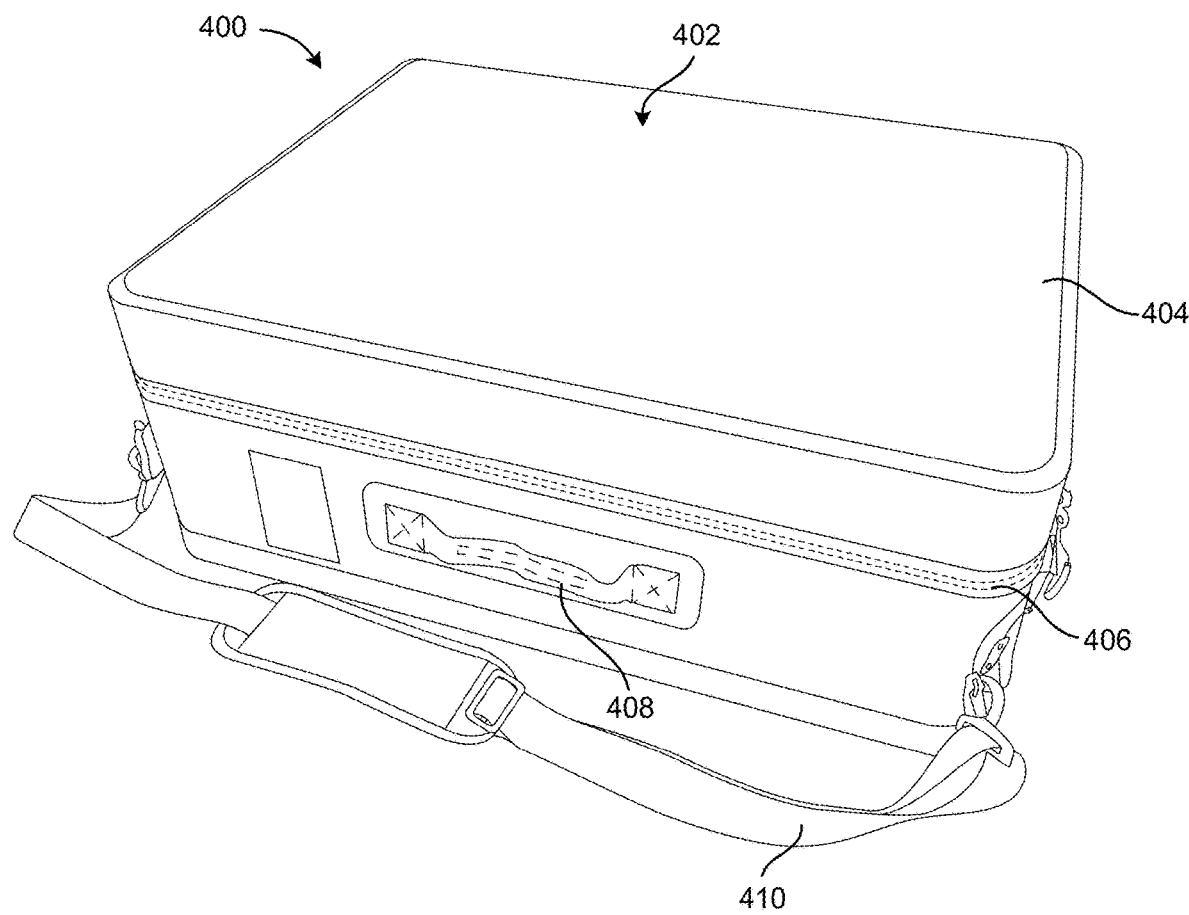
FIG. 7 is a front perspective view of another embodiment of the case of the present invention with the case in a closed state.

Referring to FIGS. 7-13, another embodiment of a carrying case 400 of the present invention is shown. As shown in FIG. 7, the case 4 includes an outer container 402 having a lid 404 that is partially removably coupled thereto with a water-resistant zipper 406. The outer container 400 also includes an outer handle 408 and a carrying strap 410 for aiding the user to transport the case 400. Optionally, rollers could be operably coupled to the outer container 402 on an outer surface thereof to further assist the user for transport. One of ordinary skill in the art will recognize that the size and shape of the outer container 402 are not limiting and therefore, the outer container 402 could be designed and manufactured in various sizes and shapes based on application.

The outer container 402 is made of a polymeric material such as silicone or plastic, with a water-resistant and shed-resistant inner surface that can be cleaned. The polymeric material enables the container 402 to be lightweight, comfortable to carry, easy to clean, and allows for a lid 404 without a separate hinge component. In other embodiments, the outer container 402 is made of metal or metal alloy such as stainless steel, or a composite material.

An optional tamper-proof seal (not shown) can be used to secure the lid 404 of the outer container 402 in a closed state, as shown in FIG. 7, and would provide a visual indication of whether the lid 404 has been opened. The tamper-proof seal may be an adhesive tape that must be removed or severed to open the lid 404. This ensures that the contents of the container 402 are not exposed to the outside environment prior to its intended use.

Alternatively, the optional tamper-proof seal could be part of the zipper 406 as a means for securing the zipper 406 closed. For example, the zipper 406 could include one or more pull tabs having holes so that a lock, e.g., combination lock, key lock or zip tie, could be secured to holes of adjacent pull tabs or between one pull tab and another engagement on the outer portion of the outer container 402.

Figure 13:
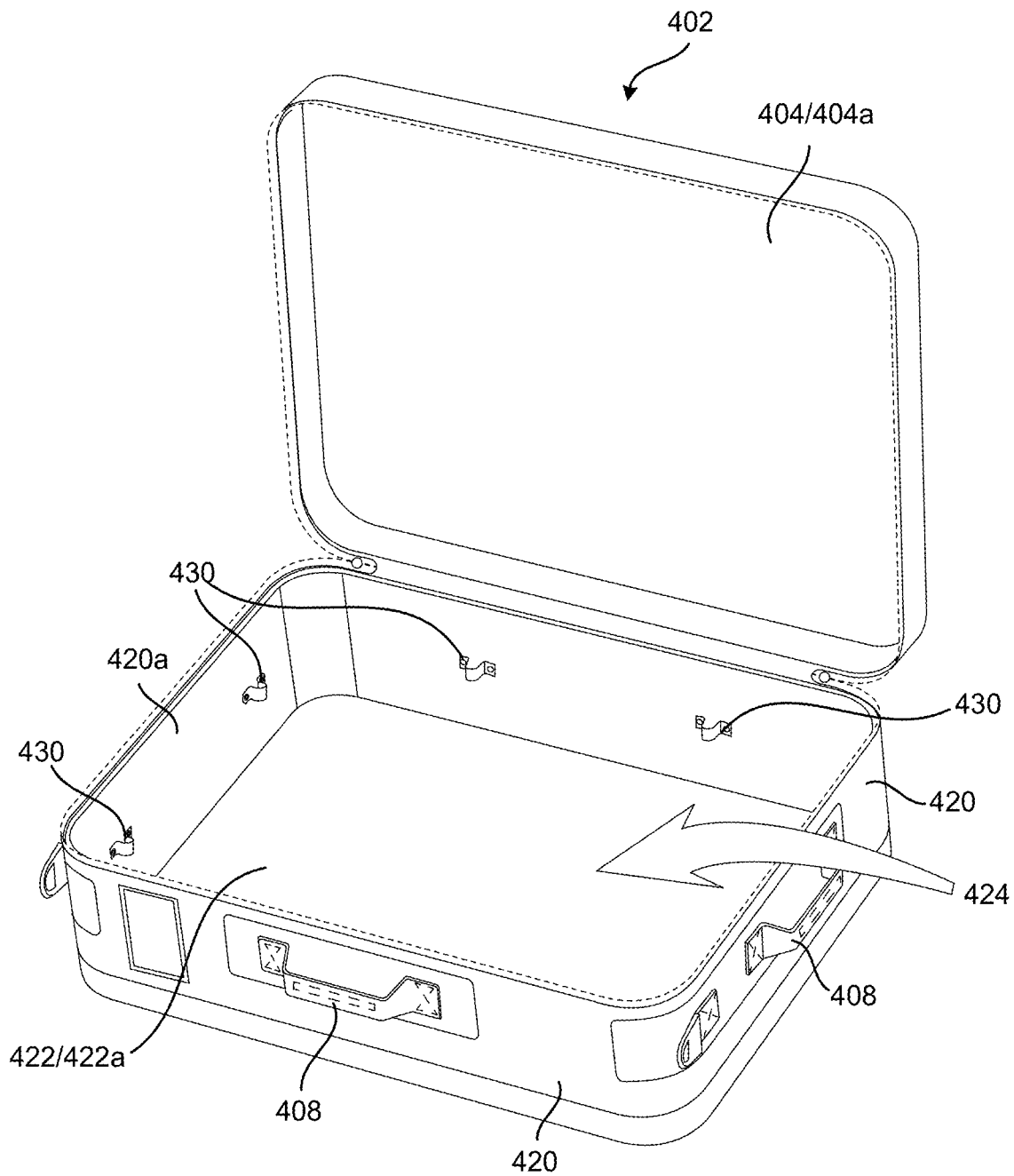
FIG. 13 shows the case of FIG. 7 in an open state with the trays removed.

Referring to FIG. 13, the outer container 402 includes side walls 420 extending from a lower support 422. Each of the side walls 420, lower support 422 and outer lid 404 are provided with an inner surface 420a, 422a and 404a, respectively, to define an interior space 424 within the outer container 402. The inner surfaces 420a, 422a, 404a are constructed of a water-resistant fabric material so that the surfaces are wipeable and washable with liquid solutions. Examples of the fabric materials are polymeric materials such as silicone, plastic and vinyl, or combinations thereof.

Figure 9:
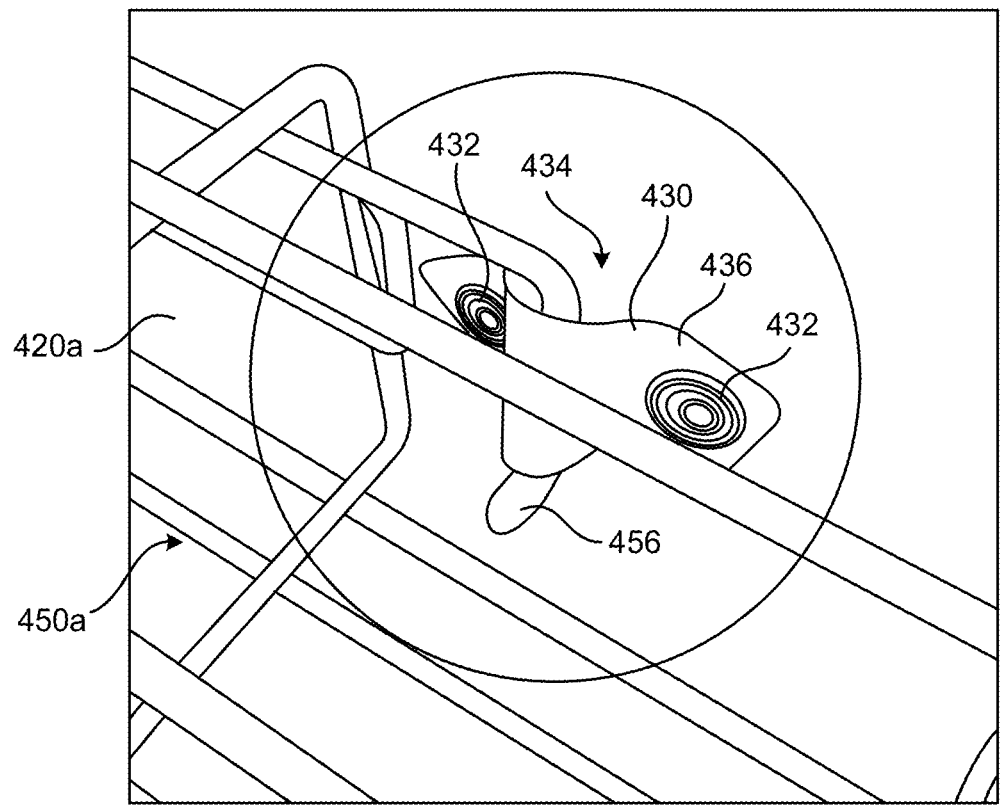
FIG. 9 shows an attachment means of the case of FIG. 7.

Referring to FIGS. 9 and 13, the interior of the outer container 402 is provided with first attachment means 430. In this embodiment, there are eight attachment means 430, two on each side wall 420, extending from the inner surfaces 420a thereof. As shown in FIG. 9, each of the first attachment means 430 in this embodiment is constructed of a flexible, yet durable, shed-resistant fabric material 436 that is fixed to the side wall 420 via rivets 432 to form a loop 434 therebetween. The fabric material is a polymeric material such as silicone, plastic and vinyl, or combinations thereof, that is capable of being cleaned with a liquid solution. The first attachment means 430 could, however, be fixed to the inner surfaces 420a by other methods. For example, instead of rivets 432, the fabric material could be attached to the inner surfaces 420a with heat welds, adhesives, screws or other types of fasteners. Other types of materials could be used for the first attachment means 430 as well. For example, the first attachment means 430 could be constructed of a coated metal similar to the inner trays, which are described in more detail below.

Figure 10:
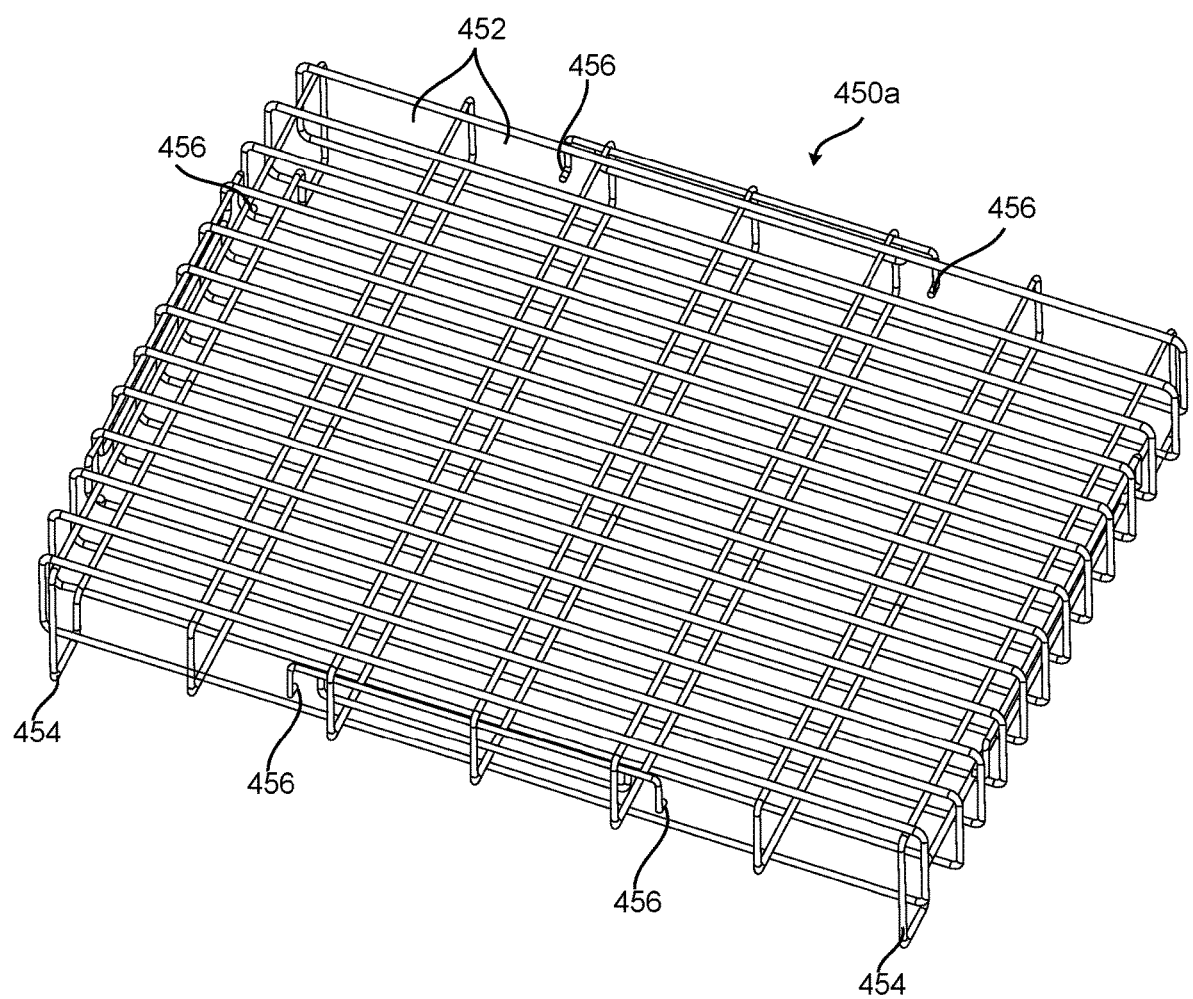
FIGS. 10-12 show embodiments of removable trays for use in the case of FIG. 7.
Figure 11:
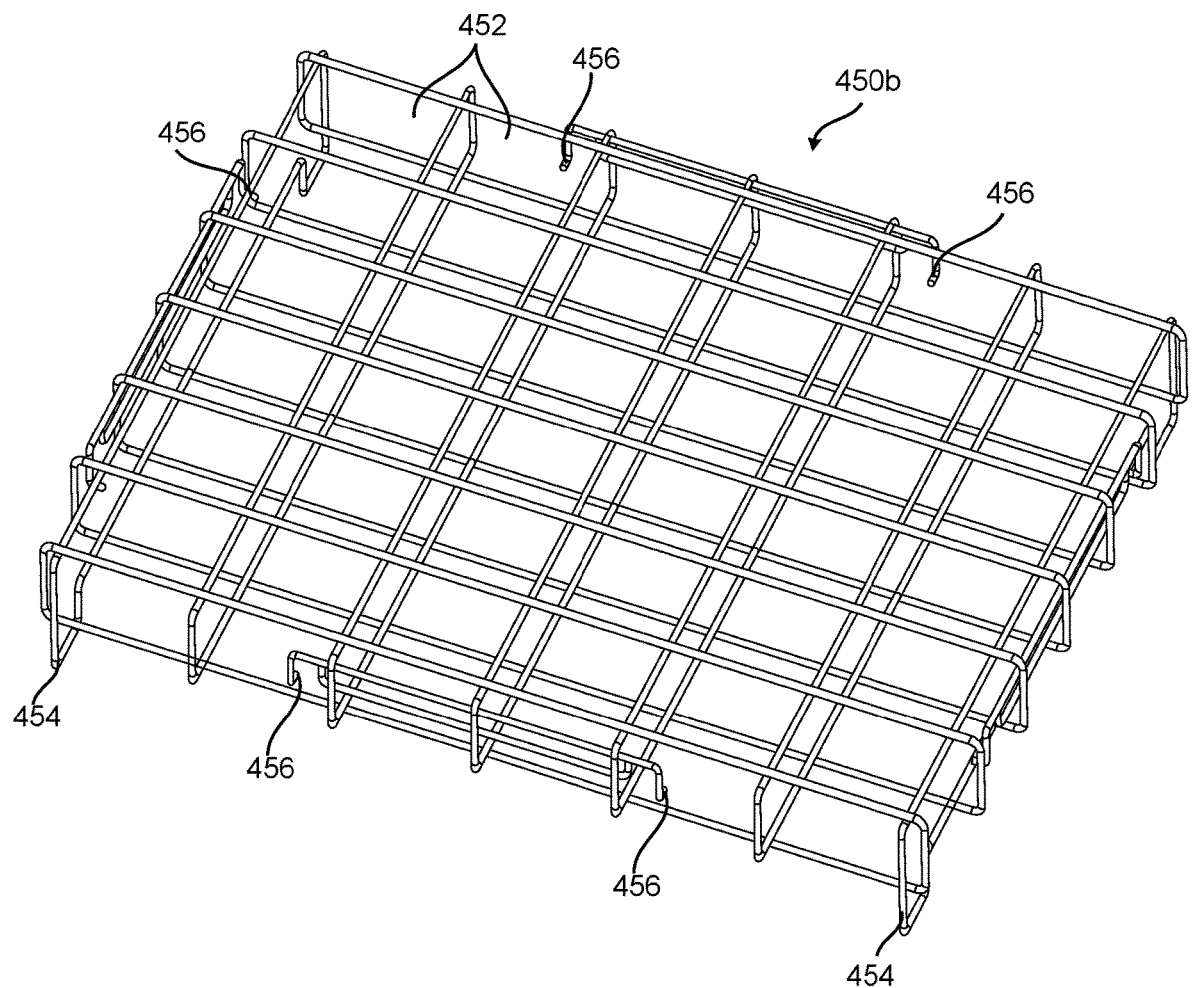
Figure 12:
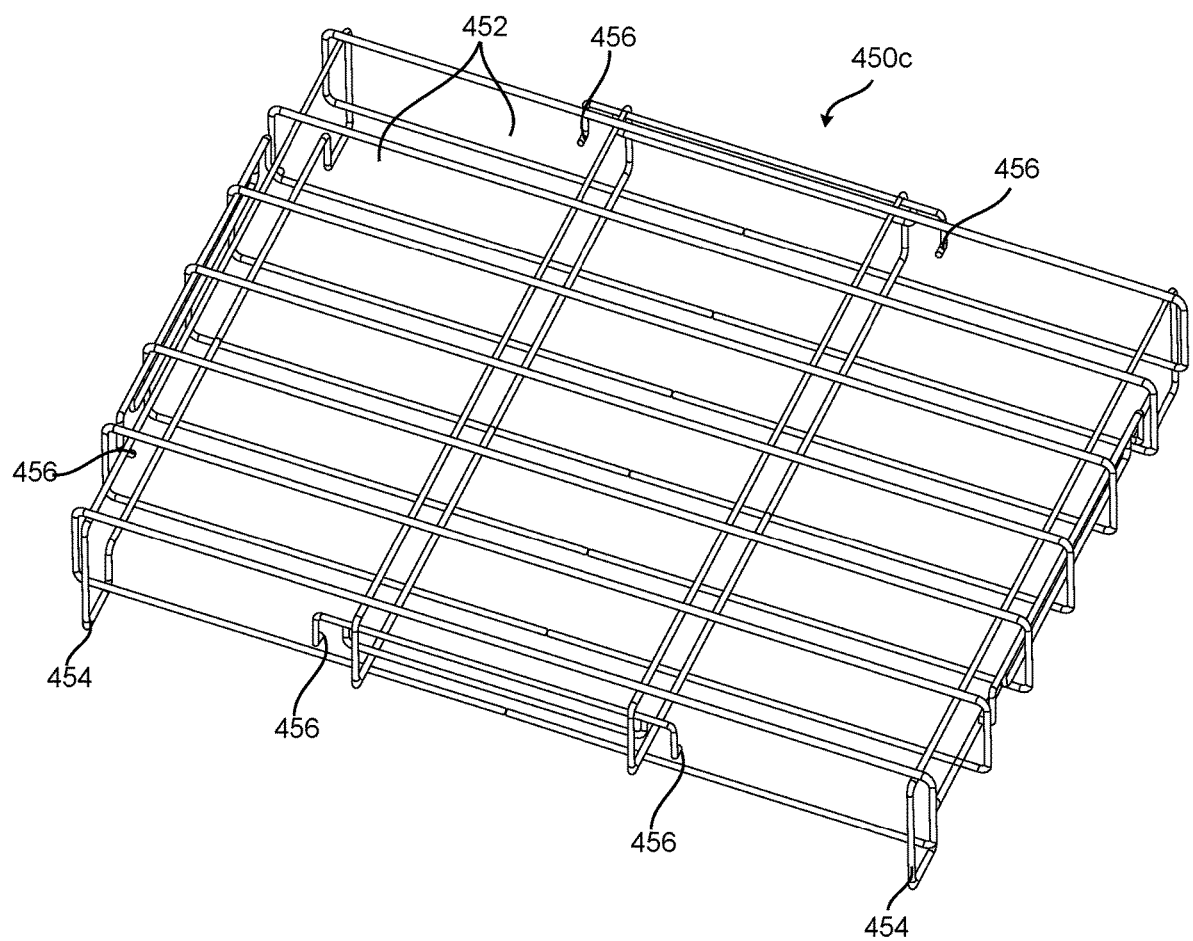

Referring to FIGS. 8-12, the case 400 includes at least one removable inner tray. In this embodiment, three inner trays 450a, 450b, 450c are provided, as shown in FIGS. 10-12, respectively, for interchangeable use. Each of the trays 450a, 450b, 450c are constructed of a coated metal and includes a plurality of inserts 452. As such, the trays 450a, 450b, 450c are shed-resistant and are capable of being easily cleaned with liquid solutions without the risk of rust or other debris forming during the cleaning process.

In one embodiment, as shown in FIG. 10, each insert 452 of the tray 450a is 3.62 inches by 1.25 inches. In another embodiment, as shown in FIG. 11, each insert 452 of the tray 450b is 4 inches by 3.62 inches. In yet another embodiment, as shown in FIG. 12, each insert 452 of the tray 450c is 7.38 inches by 2.62 inches. Each tray 450a, 450b, 450c is interchangeable for use with the case 400 depending on the size of the materials being stored and transported. Alternatively, a single tray with a variety of sizes of inserts could be provided to accommodate for different sizes of the materials being stored and transported. One of ordinary skill in the art will recognize that the sizes and shapes of the inner trays 450a-c and inserts 452 therein are not limiting and therefore, the inner trays 450a-c and inserts 452 could be designed and manufactured in various sizes and shapes based on application. For example, the inner tray could be an "air cell" with one insert therein to accommodate one large object.

Referring to FIGS. 10-12, each tray 450a-c includes a base 454 for securing the tray 450a-c to the lower support 422 of the container 402. Each tray 450a-c is also provided with second attachment means 456 corresponding to the locations of the first attachment means 430 of the outer container 402. In this embodiment, as shown in more detail in FIG. 9, the second attachment means 456 is a hook extending from the tray 450a-c. That is, hooks extend inwardly toward the tray 450a-c so that each hook is secured to a corresponding loop of the first attachment means 430. With such configuration, the tray 450a-c is sufficiently secured to the container 402 during transport and is also easily removable during cleaning. The second attachment means 456 could take on other forms as well. For example, the tray 450a-c could be provided with a hook-and-loop fastener or a zip tie for engaging and securing to the first attachment means 430.

Figure 8:
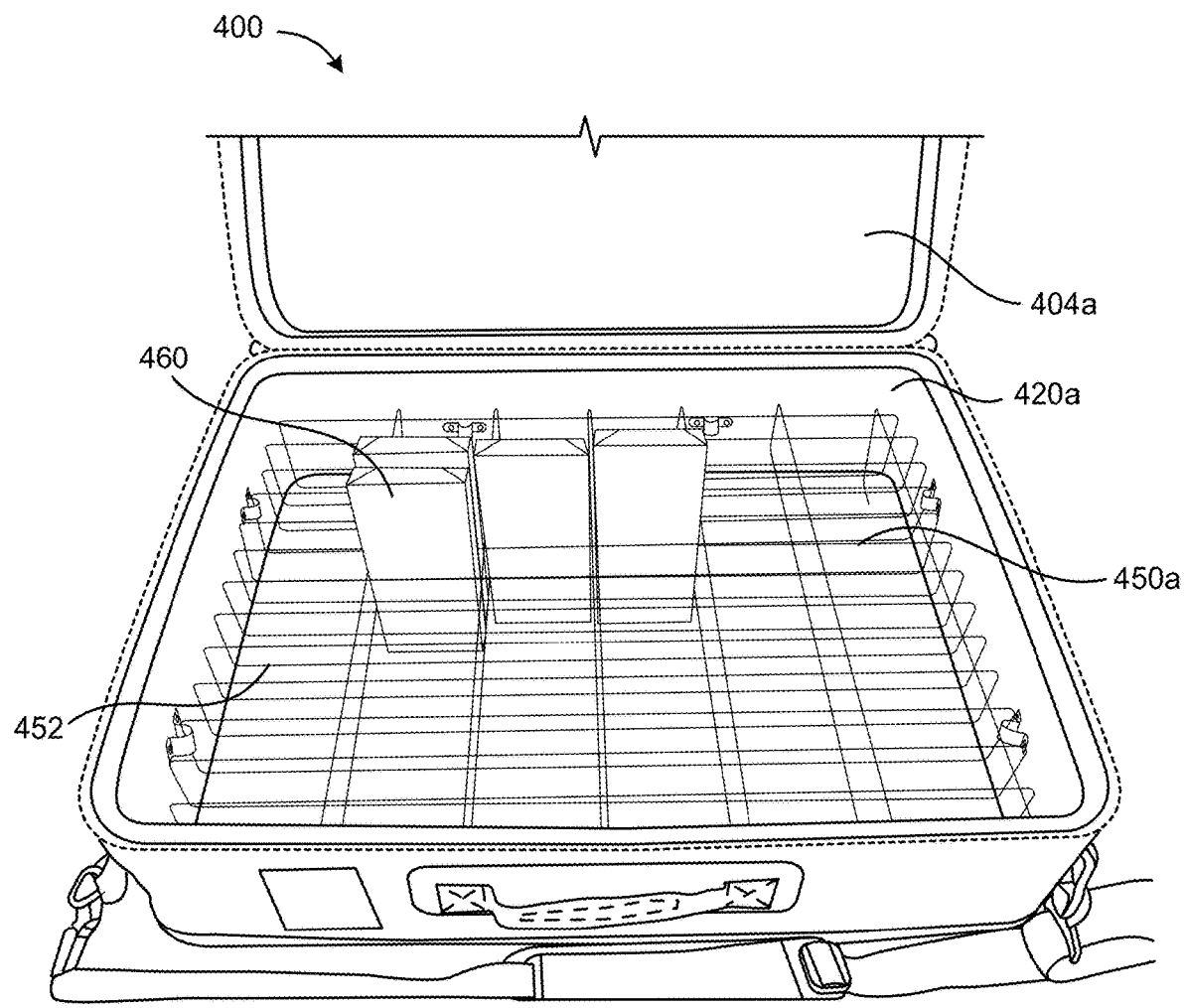
FIG. 8 is a front perspective view of the case of FIG. 7 in an open state.

In operation, as shown in FIG. 9, the tray 450a-c is secured to the container 402 by engaging the hooks 456 to the loops 430 of the outer container 402. Materials 460 are positioned within the inserts 452, as shown in FIG. 8. The lid 404 is closed and secured in a closed state with the zipper 406, as shown in FIG. 7. The case 400 is capable of being transported while the materials 460 within remain secure within the inserts 452 while they are protected from the outside environment.

As such, the case of the present invention provides a solution for transporting sterile objects, including transporting entire cases or trays of the sterile objects into a sterile environment, while minimizing the risk of contamination of a sterile environment. The case of the present invention could be used in a variety of applications, including, but not limited to, hospitals, research centers and forensic laboratories.

The present invention may be embodied in other specific forms without departing from its spirit or essential characteristics. The described embodiments are to be considered in all respects only as illustrative and not restrictive. The scope of the invention will be, therefore, indicated by claims rather than by the foregoing description. All changes, which come within the meaning and range of equivalency of the claims, are to be embraced within their scope.

What is claimed is:

1. A carrying case comprising:
   an outer container having:
   a plurality of side walls extending from a lower support;
   an outer lid at least partially removably coupled with the plurality of side walls and positioned opposite the lower support, each of the side walls, lower support and outer lid having an inner surface and an outer surface, the inner surfaces of the side walls, lower support and outer lid defining an interior space within the case; and a plurality of first attachment means extending from at least two opposing side wall inner surfaces; and a removable inner tray having:
    a plurality of inserts, the plurality of inserts configured to fit within the interior space of the outer container; and
    a plurality of second attachment means extending from the plurality of inserts, each of the second attachment means positioned to correspond with locations of the first attachment means such that the first and second attachment means are engaged when the inner tray is positioned within the interior space of the case;

wherein the first attachment means is a loop formed with a flexible fabric material and the second attachment is a hook.

2. The carrying case of claim 1, wherein the outer lid is coupled with the plurality of side walls by a water-resistant zipper.

3. The carrying case of claim 1, wherein the outer container is composed of a material selected from a polymeric material, metal, and/or a composite material.

4. The carrying case of claim 3, wherein the polymeric material is selected from silicone, plastic, and vinyl.

5. The carrying case of claim 3, wherein the metal is selected from aluminum and stainless steel.

6. The carrying case of claim 1, wherein the inner surfaces of the side walls, lower support and outer lid are water-resistant and shed-resistant.

7. The carrying case of claim 1, wherein the outer surface of the outer container is constructed of a water-resistant material.

8. The carrying case of claim 1, further comprising an outer handle coupled to the outer surface of the outer container.

9. The carrying case of claim 1, further comprising a carrying strap coupled to the outer surface of the outer container.

10. The carrying case of claim 1, wherein the inner tray is constructed of a coated metal.

11. A carrying case comprising:
an outer container having:
    a plurality of side walls extending from a lower support;
    an outer lid positioned opposite the lower support and at least partially removably coupled with the plurality of side walls with a water-resistant zipper, each of the side walls, lower support and outer lid having an inner surface and an outer surface, the inner surfaces of the side walls, lower support and outer lid defining an interior space within the case, wherein the inner surfaces of the side walls, lower support and outer lid are water-resistant and shed-resistant; and
    a plurality of first attachment means extending from at least two opposing side wall inner surfaces; and
a removable inner tray having:
    a plurality of inserts, the plurality of inserts configured to fit within the interior space of the outer container, the plurality of inserts constructed of a coated metal; and
    a plurality of second attachment means extending from the plurality of inserts, each of the second attachment means positioned to correspond with locations of the first attachment means such that the first and second attachment means are engaged when the inner tray is positioned within the interior space of the case.

12. The carrying case of claim 1, wherein the first attachment means is a loop formed with a flexible fabric material and the second attachment is a hook.

13. The carrying case of claim 1, wherein the outer container is composed of a material selected from a polymeric material, metal, and/or a composite material.

14. The carrying case of claim 12, wherein the polymeric material is selected from silicone, plastic, and vinyl.

15. The carrying case of claim 12, wherein the metal is selected from aluminum and stainless steel.

16. The carrying case of claim 11, wherein the outer surface of the outer container is constructed of a water-resistant material.

17. A carrying case comprising:
an outer container having:
    a plurality of side walls extending from a lower support;
    an outer lid at least partially removably coupled with the plurality of side walls and positioned opposite the lower support, each of the side walls, lower support and outer lid having an inner surface and an outer surface, the inner surfaces of the side walls, lower support and outer lid defining an interior space within the case; and
    a plurality of first attachment means extending from at least two opposing side wall inner surfaces, the first attachment means being a loop formed with a flexible fabric material; and
a removable inner tray having:
    a plurality of inserts, the plurality of inserts configured to fit within the interior space of the outer container; and
    a plurality of second attachment means extending from the plurality of inserts, the second attachment means being a hook, each of the second attachment means positioned to correspond with locations of the first attachment means such that the first and second attachment means are engaged when the inner tray is positioned within the interior space of the case.

18. The carrying case of claim 17, wherein the outer lid is coupled with the plurality of side walls by a water-resistant zipper.

19. The carrying case of claim 17, wherein the inner surfaces of the side walls, lower support and outer lid are water-resistant and shed-resistant.

\* \* \* \* \*